United States Patent [19]
Seguin et al.

[11] Patent Number: 6,001,389
[45] Date of Patent: Dec. 14, 1999

[54] COMPOSITIONS CONTAINING BIOLOGICALLY ACTIVE SILICON

[76] Inventors: Marie-Christine Seguin; Jean Gueyne, both of 44, Bolevard d'Italie - MC 98000, Monaco, Monaco

[21] Appl. No.: 09/046,511

[22] Filed: Mar. 24, 1998

[30] Foreign Application Priority Data

Mar. 24, 1997 [FR] France .................................... 97 03793

[51] Int. Cl.$^6$ ................................. C07F 7/02; C07F 7/08; C07F 7/18; A61K 31/695; A61K 7/48
[52] U.S. Cl. ......................... 424/434; 424/433; 424/436; 424/400; 514/63
[58] Field of Search .............................. 514/63; 424/400, 424/434, 433, 436

[56] References Cited

U.S. PATENT DOCUMENTS

| | | | |
|---|---|---|---|
| 3,914,416 | 10/1975 | Gueyne et al. | 424/184 |
| 4,985,405 | 1/1991 | Gueyne et al. . | |

FOREIGN PATENT DOCUMENTS

| | | |
|---|---|---|
| 0 525 573 | 2/1993 | European Pat. Off. . |
| 0 525 573 A1 | 2/1993 | European Pat. Off. . |
| 1 177 091 | 4/1959 | France . |
| 6 871 M | 4/1969 | France . |
| 96/10574 | 4/1996 | WIPO . |
| 96/10575 | 4/1996 | WIPO . |

OTHER PUBLICATIONS

Henrotte et al., "Le rôle régulateur du silicium dans la division cellulaire," 306 *C.R. Acad. Sci.*, 525–528 (1988) with English Abstract.

*Primary Examiner*—Thurman K. Page
*Assistant Examiner*—Brian K. Seidleck
*Attorney, Agent, or Firm*—Lydon & Brown, LLP

[57] ABSTRACT

A method of treatment of osteo-articular disease which includes administering an effective amount of a pharmaceutical composition containing a compound of specified formula and an excipient to a patient in need of such treatment. The compounds of specified formula have a phosphonate group on one end and a silanol or silanol precursor on the opposite end, and can inhibit serine proteases.

8 Claims, No Drawings

COMPOSITIONS CONTAINING BIOLOGICALLY ACTIVE SILICON

FIELD OF THE INVENTION

The present invention concerns new pharmaceutical and cosmetic compositions capable of inhibiting serine proteases and containing at least one compound made of biologically active silicon.

BACKGROUND OF THE INVENTION

The compounds containing biologically active silicon are organo silicon compounds and more especially silanols bearing numerous Si—OH bonds. Silanols are described in the state of the art as constituting a form of silicon assimilable by the organism, given that they have the property of existing as soluble oligomer form in aqueous solution with a low molecular weight (EP-0 289 366).

Numerous complexes of silanols having interesting pharmaceutical properties have already been described in the past. The French special patent on drug N° 6.871 M which has been registered on Dec., 23rd, 1996, describes an organo silicic complex used as drug against all inflammatory phenomena. FR-A-2725207 describes silanols precursors which are compounds made of silicon bearing biologically hydrolyzable bonds notably in contact with alive tissue and enabling the release of oligomers having biologically active Si—OH functions.

Silanols, thus obtained in vivo are pharmaceutically usefull, particularly for the treatment of arthritis, for the restructuration of micro-vessels, for the treatment of the sportsman tendinitis, for the treatment of asthenia, for the treatment of cataract, for the treatment of arteriopatia such as notably arteriosclerosis and more generally for their anti-inflammatory, anti-edematous, anti-glycation, antiradical, analgesic, regenerating and repairing activities.

Silanols of the anterior art are administered via general, orally or paranterally, and act in a non specific way.

To notably remedy this drawback, the main goal of the present invention is to propose a pharmaceutical composition, capable of inhibiting serine proteases, containing a compound made of biologically active silicon capable of aiming in the organism a tissue or a specific organ, such as particularly the osseous or cartilaginous tissue, or cutaneous tissue and exhibit on these tissue a pharmacological activity.

SUMMARY OF THE INVENTION

The pharmaceutical composition according to the invention includes, in association with any suitable excipient, at least one compound of the following general formula (I):

$$R_6R_7P(O)\text{—}(CHR_5)_m\text{—}(CHR_4)_n\text{—}Si(OR_1)(OR_2)(R_3) \qquad (I)$$

in which:

$R_1$ and $R_2$ each one independently represent an hydrogen atom or an alkyl group, $R_3$ represents an hydroxyl group or an alcoxy group or an alkyl group, $R_4$ and $R_5$ represent each one independently an hydrogen group, an hydroxyl group, an alkyl group or an acid carboxylic function, $R_6$ and $R_7$ represent each one independently an alcoxy group, n is a whole number superior or equal to 0 and inferior or equal to 4, m is a whole number strictly superior to 0 and inferior or equal to 3.

DETAILED DESCRIPTION OF THE PREFERRED EMBODIMENTS:

Advantageously, the pharmaceutical composition according to the invention includes a compound of formula (I) in which:

$R_1$ and $R_2$ each one independently represent an hydrogen atom or an alkyl group, $R_3$ represents an hydroxyl group or an alcoxy group or an alkyl group, $R_4$ and $R_5$ represent each one independently an hydrogen group or an hydroxyl group, $R_6$ and $R_7$ represent each one independently an alcoxy group, n is a whole number superior or equal to 0 and inferior or equal to 4, m is a whole number strictly superior to 0 and inferior or equal to 3.

and the sum (m+n) is strictly inferior to 6.

Among these compounds, are preferred the compounds of formula (I) in which:

$R_1$ and R2 each one independently represent an hydrogen atom or a $C_{1-4}$ alkyl group, $R_3$ represents an hydroxyl group or an alcoxy group or a $C_{1-4}$ alkyl group, $R_4$ and $R_5$ represent each one independently an hydrogen group or an hydroxyl group, $R_6$ and $R_7$ represent each one independently a $C_{1-4}$ alcoxy group, n is a whole number superior or equal to 0 and inferior or equal to 4, m is a whole number strictly superior to 0 and inferior or equal to 3.

and the sum (m+n) is strictly equal to 2.

According to a preferred embodiment of the invention, the compound of formula (I) contained in the pharmaceutical composition according to the invention is the diethylphosphatotriethoxysilane.

Advantageously, the pharmaceutical composition according to the invention is administered orally, rectally or topically.

According to a special embodiment, the pharmaceutical composition according to the invention is in solid form.

According to an other special embodiment, the excipient bears numerous hydroxyl functions. Preferably, the excipient is lactose.

Another goal of the invention is to propose a drug for the treatment of arthritis, osteoporosis, chronic evolutive polyarthritis, Paget disease, or cutaneous affections, notably eczematiform, capable of inhibiting serine proteases, which includes the pharmaceutical composition described hereabove.

The invention is illustrated on a non-limitative basis, with the following detailed description and examples:

Thus, the composition according to the invention includes a compound of formula (I) which is a molecule having two main groups: on one end a phosphonate group and on the other hand a silanol group or a silanol precursor. This compound is such as the P-C bond is not hydrolyzable in vivo and the Si—C bond is not hydrolyzable in vivo.

It can be noticed a real synergy between both groups, and it leads to the obtention of a very specific targetting effect for the compound according to the invention and an increased efficiency of the silanol function at the target level.

The phosphonate group will help in carrying the compound according to the invention at the tissue level rich in phosphates, i.e. the bone and the cartilage, and the silanol group will thus act on the metalloproteases present in the extra cellular matrix. It is to be noted that the metalloproteases inhibition using compositions according to the invention is not specific of a particular tissue, and thus will be able to have extremely wide and various applications, on all pathologies that are accompanied by an over activity of the metalloproteases.

Another function of the phosphonate group is to act as a buffer agent at the target level.

On the other hand, since the P-C bond is not hydrolyzable in vivo, the phosphonate group is not released at the tissue level. Thus, it cannot be incorporated by the organism in the osseous matrix and cannot accumulate in the bone.

The pharmaceutical compositions according to the invention are therefore especially appreciated for their ability to aim a specific target, site of a pathology, and for their ability to non ubiquitously distribute at the level of the extracellular matrix.

According to an advantageous alternative version of the invention, the pharmaceutical compositions include a compound of general formula (I) in which $R_4$ and $R_5$ are both independently an hydrogen atom or an hydroxyl group, and the (m+n) sum is strictly inferior to 6. As a matter of fact, it has been noticed that a long central chain can represent a steric factor able to diminish the access of the compound according to the invention on the action site. Besides, if the central chain is a succession of apolar groups, such as notably methylene groups, the solubility of the compound according to the invention can strongly diminish, which makes it less assimilable and thus less active.

According to another advantageous alternative version of the invention, the pharmaceutical composition includes a compound of general formula (I) in which $R_4$ and $R_5$ are both independently an hydrogen atom or an hydroxyl group and the (m+n) sum is equal to 2.

A preferred pharmaceutical composition is the composition containing diethylphosphatoethyltriethoxysilane with the following formula:

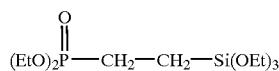

The pharmaceutical composition can be administered orally, rectally or topically, orally being preferred; it is preferably in solid form.

As a matter of fact the desired goal is to obtain a pharmaceutical composition containing a compound of formula (I) which must be solid, unidose and administered orally, in order to be used in ambulatory medication which does not require the realization of previous medical treatment.

In the pharmaceutical composition, the appropriate excipient associated to the compound of formula (I) can be any excipient pharmaceutically acceptable. Preferably, the excipient which is used has numerous hydroxyl functions. The preferred excipient is lactose.

The pharmaceutic compositions according to the invention are advantageously used in order to obtain drugs for the treatment of osteo-articular diseases, such as particularly arthrosis, osteoporosis, evolutive chronic polyarthritis, Paget disease, or cutaneous afflictions, notably eczematiform.

The compounds of the general formula (I) do not act directly but inderectly at the level of the extra cellular matrix as inhibitory agents of the metalloproteases.

For example, the use of compounds according to the invention is studied on the metalloproteases activity such as collagenase, stromelysin and chymotrypsine, at the level of the chondrocytes, the osteoblasts or the epidermis.

We would like to remind that chondrocytes are cartilaginous cells present in the extra cellular matrix. They produce proteolitic enzymes and notably metalloproteases (stromelysin and collagenase) able to digest the cartilaginous matrix. Under normal situation, there is an equilibrium between the chondroresorption and the chondroformation. A significant increase of the metalloproteases activity creates an unbalance inducing a massive chondroresorption. This metalloproteases' over activity is at the origin of arthritis. It is notably induced and regulated in an autocrine and paracrine way by the means of information mediators cytokines, and more especially by interleukine-1 (IL-1) which is one of the most active cytokine during the cartilage degradation process.

The use of these compounds of general formula (I) according to the invention, enables to inhibit the metalloproteases' activity and more especially the one of the serine proteases, at the basal level as well as in the situation of interleukine-dependent over activation (examples 6 and 7).

Besides, we would like to remind that the extra cellular matrix of an epidermis is said to be a compartment where proteolysis reactions occur, due, among others, to enzymes from the serine proteases' family (trypsine, chymotrypsine, urokinase-like, desquamine). These hydrolysis reactions are implicated in the epidermis catabolic activity and in several other equilibria such as hydration, desquamation or inflammation.

We have notably noticed the increase of enzymes activity on the skin after an oxidative stress, such as notably a sunburn.

Desquamine is a serine-protease very similar to urokinase. We know that this enzyme is able to hydrolyze the keratinocytes' desmosomes and thus to modulate the skin's desquamation. This enzyme is also said to be implicated in the release control of IL-1 from Pro-IL-1 mainly localized in the hemi-desmosomes (Forestier & Sauder 1988). But the use of the compounds of the general formula (I) according to the invention, enables to inhibit the desquamine's activity in an epidermic extract (example 10), thus, to diminish the IL-1 release (responsible for the cartilage's inflammation and degradation) from Pro-IL-1. Thus, the compounds according to the invention can be validly used for the treatment and prevention of chronic pathologies.

The following examples are illustrative (but not restrictive):

EXAMPLE 1

Effect of a diethylphosphatoethyltrisilanol's precursor, the diethylphosphatoethyltriethoxysilane, on the collagenase type activity of human chondrocytes culture.

Chondrocytes cultures are carried out from human cartilages sampled on cadavers 12 hours after the death. In aqueous buffered medium (pH 7.0–7.4), the diethylphosphatoethyltriethoxysilane releases the corresponding diethylphosphatoethyltrisilanol, which is the active silanol. The collagenase type enzymatic activity of these chondrocytes cultures is quantified following the Cawston and Barrett method. Under the silanol's effect, a dose-dependent decrease of the "collagenase-like" activity of the chondrocytes is observed (30% inhibition for 500 μg/ml diethylphosphatoethyltrisilanol).

EXAMPLE 2

Effect of a diethylphosphatoethyltrisilanol's precursor, the diethylphosphatoethyltriethoxysilane, on the collagenase type activity of human chondrocytes cultures after IL-1 induction.

Chondrocytes cultures are carried out from human cartilages sampled on cadavers 12 hours after the death. In aqueous buffered medium (pH 7.0–7.4), the diethylphosphatoethyltriethoxysilane releases the corresponding diethylphosphatoethyltrisilanol, which is the active silanol. The collagenase type enzymatic activity of these chondrocytes cultures is quantified following the Cawston and Barrett method after previous treatment of the cultures by IL-1. Under the silanol's effect, a dose-dependent decrease of the "collagenase-like" activity of the chondrocytes is observed (21% inhibition for 500 μg/ml diethylphosphatoethyltrisilanol).

EXAMPLE 3

Effect of a diethylphosphatoethyltrisilanol's precursor, the diethylphosphatoethyltriethoxysilane, on the stromelysine type activity of human chondrocytes culture.

Chondrocytes cultures are carried out from human cartilages sampled on cadavers 12 hours after the death. In aqueous buffered medium (pH 7.0–7.4), the diethylphosphatoethyltriethoxysilane releases the corresponding diethylphosphatoethyltrisilanol, which is the active silanol. The stromelysine type enzymatic activity of these chondrocytes cultures is quantified by the method of digestion of casein coupled with resorufine. Under the silanol's effect, a dose-dependent decrease of the "collagenase-like" activity of the chondrocytes is observed (37% inhibition for 500 μg/ml diethylphosphatoethyltrisilanol).

EXAMPLE 4

Effect of a diethylphosphatoethyltrisilanol's precursor, the diethylphosphatoethyltriethoxysilane, on the stromelysine type activity of human chondrocytes culture after IL-1 induction.

Human chondrocytes cultures are carried out from human cartilages sampled on cadavers 12 hours after the death. In aqueous buffered medium (pH 7.0–7.4), the diethylphosphatoethyltriethoxysilane releases the corresponding diethylphosphatoethyltrisilanol, which is the active silanol. The stromelysine type enzymatic activity of these chondrocytes cultures is quantified, after previous treatment of cultures with IL-1, by the method of digestion of casein coupled with resorufine. Under the silanol's effect, a dose-dependent decrease of the "collagenase-like" activity of the chondrocytes is observed (18% inhibition for 500 μg/ml diethylphosphatoethyltrisilanol).

EXAMPLE 5

Effect of a diethylphosphatoethyltrisilanol's precursor, the diethylphosphatoethyltriethoxysilane, on the "desquame-like" activity of an epidermic extract.

Desquamine is obtained from an epidermic extract according to the Brysk and al (1994) method. The desquamine activity is evaluated by its ability to hydrolyze the synthetic specific substrate of the tPA for which it has a very strong affinity. After previous treatment of the epidermic extract by the silanol, a dose-dependent inhibition of the "desquamine-like" activity of the epidermic extract is observed (25% inhibition for 300 μg/ml de $CH_3Si(OH)_3$).

EXAMPLE 6

Effect of a diethylphosphatoethyltrisilanol's precursor, the diethylphosphatoethyltriethoxysilane, on the synthetic activity of osteoblasts.

Osteoblasts cultures are carried out from human bones sampled on cadavers 12 hours after the death. In aqueous buffered medium (pH 7.0–7.4), the diethylphosphatoethyltriethoxysilane releases the corresponding diethylphosphatoethyltrisilanol, which is the active silanol. The synthetic activity of these osteoblasts is quantified by the measure of the alkaline phosphatase activity. Under the diethylphosphatoethyltrisilanol's effect, a dose-dependent increase of the osteoblasts alkaline phosphatases activity is observed (+24% inhibition for 100 μg/ml diethylphosphatoethyltrisilanol).

EXAMPLE 7

Effect of a diethylphosphatoethyltrisilanol's precursor, the diethylphosphatoethyltriethoxysilane, on the IL-6 activity of osteoblasts.

Osteoblasts cultures are carried out from human bones sampled on cadavers 12 hours after the death. In aqueous buffered medium (pH 7.0–7.4), the diethylphosphatoethyltriethoxysilane releases the corresponding diethylphosphatoethyltrisilanol, which is the active silanol. IL-6 is quantified by the ELISA technique. Under the diethylphosphatoethyltrisilanol's effect, a dose-dependent decrease of the osteoblasts IL-6 level is observed (−49% inhibition for 100 μg/ml diethylphosphatoethyltrisilanol).

EXAMPLE 8

Effect of a diethylphosphatoethyltrisilanol's precursor, the diethylphosphatoethyltriethoxysilane, on the chymotrypsine type activity of an epidermic extract.

After sampling from a cutaneous tissue, the epidermis is cut then put in an appropriate buffered solution. The solution is homogenized with Ultra Turax (40 C.) until a satisfying epidermic extract is obtained. The chymotrypsine-like activity of this extract is assessed by the measure of the N alpha-Benzoyl-L-Tyrosine Ethyl Ester (BTEE) degradation (specific synthetic substrate). Under the diethylphosphatoethyltrisilanol's effect, a dose-dependant decrease of the "chymotrypsine-like" activity of the epidermic extract is observed (27% inhibition for 400 μ0 g/ml diethylphosphatoethyltrisilanol).

We claim:

1. Pharmaceutical composition comprising a compound of the following general formula (I):

$$R_6R_7P(O)-(CHR_5)_m-(CHR_4)_n-Si(OR_1)(OR_2(R_3) \qquad (I)$$

in which:

$R_1$ and $R_2$ are each an ethyl group, $R_3$ is an ethyloxy group, $R_4$ and $R_5$ are each a hydrogen atom, $R_6$ and $R_7$ are each an ethyloxy group, n is 1, m 1, in an amount effective to inhibit serine proteases and a pharmaceutically acceptable excipient.

2. Pharmaceutical composition according to claim 1 characterized in that it is administered orally, rectally or topically.

3. Pharmaceutical composition according to claim 1 characterized in that it is in solid form.

4. Pharmaceutical composition according to claim 1 characterized in that it that the excipient bears several hydroxyl functions.

5. Pharmaceutical composition according to the claim 4 characterized in that the excipient is lactose.

6. A method of treatment of osteo-articular disease, or cutaneous affliction comprising administering an amount of a pharmaceutical composition according to claim 1 which is effective to inhibit serine proteases to a patient in need of said treatment.

7. The method of claim 6, wherein said osteo-articular diesase is selected from the group consisting of arthrosis, osteroporosis, evolutive chronic polyarthritis and Pagent disease.

8. The method of claim 6, wherein said cutaneous affliction is eczematiform.

* * * * *